US005538669A

United States Patent [19]

Schulz et al.

[11] Patent Number: 5,538,669

[45] Date of Patent: Jul. 23, 1996

[54] STABILIZED SURFACTANT PASTE

[75] Inventors: Paul Schulz, Wuppertal; Rainer Eskuchen, Duesseldorf; Manfred Weuthen, Solingen, all of Germany

[73] Assignee: Henkel Kommanditgesellschaft auf Aktien, Duesseldorf, Germany

[21] Appl. No.: 424,230

[22] Filed: Apr. 19, 1995

Related U.S. Application Data

[63] Continuation of Ser. No. 50,322, filed as PCT/EP91/02073, Nov. 4, 1991, abandoned.

[30] Foreign Application Priority Data

Nov. 9, 1990 [DE] Germany .......................... 40 35 722.8

[51] Int. Cl.[6] .............................. B01F 17/56; C07H 1/06

[52] U.S. Cl. .......................... 252/351; 536/127; 510/470; 510/535

[58] Field of Search .................................... 252/351, 156, 252/DIG. 1, DIG. 6, DIG. 14; 536/18.6, 127

[56] References Cited

U.S. PATENT DOCUMENTS

| | | | |
|---|---|---|---|
| 3,415,753 | 12/1968 | Stein et al. | 252/121 |
| 3,450,690 | 6/1969 | Gibbons et al. | 536/18.5 |
| 3,547,828 | 12/1970 | Mansfield et al. | 252/351 |
| 3,839,318 | 10/1974 | Mansfield | 536/18.6 |
| 4,147,652 | 4/1979 | Kaniecki | 252/DIG. 1 |
| 4,510,306 | 4/1985 | Langdon | 536/127 |
| 4,557,729 | 12/1985 | McDaniel, Jr. et al. | 8/111 |
| 4,599,188 | 7/1986 | Llenado | 252/DIG. 14 |
| 4,780,234 | 10/1988 | Malik et al. | 252/DIG. 14 |
| 4,898,934 | 2/1990 | Lueders et al. | 536/18.6 |
| 4,959,468 | 9/1990 | Ravi et al. | 536/127 |
| 5,130,420 | 7/1992 | Yamamuro et al. | 536/18.6 |
| 5,138,046 | 8/1992 | Wuest et al. | 536/18.6 |
| 5,205,959 | 4/1993 | Schmid et al. | 252/156 X |

FOREIGN PATENT DOCUMENTS

| | | |
|---|---|---|
| 0301298 | 7/1988 | European Pat. Off. . |
| 0357969 | 8/1989 | European Pat. Off. . |
| 0362671 | 9/1989 | European Pat. Off. . |
| 0355551 | 2/1990 | European Pat. Off. . |
| 1254798 | 6/1964 | Germany . |
| 4017922 | 6/1990 | Germany . |

*Primary Examiner*—Richard D. Lovering
*Attorney, Agent, or Firm*—Wayne C. Jaeschke; John E. Drach; Henry E. Millson, Jr.

[57] ABSTRACT

Water-based surfactant pastes, more particularly those containing nonionic surfactants of the alkyl glycoside type, are effectively stabilized against microbial infestation if, after oxidative bleaching to eliminate alkali-sensitive color bodies, they are adjusted to a pH value of at least 11 by addition of alkaline substances.

21 Claims, No Drawings

STABILIZED SURFACTANT PASTE

This application is a continuation of application Ser. No. 08/050,322, filed as PCT/EP91/02073, Nov. 4, 1991, and now abandoned.

BACKGROUND OF THE INVENTION

1. Field of the Invention

This invention relates to a water-based surfactant paste stabilized against microbial infestation, the surfactant in particular essentially consisting of a nonionic surfactant of the alkyl glycoside type. The invention also relates to a process for the production of the surfactant paste.

2. Statement of Related Art

The surfactants present in modern detergents and cosmetic cleansing preparations have to satisfy stringent requirements in regard to biological degradability. Such surfactants are often marketed in the form of water-based preparations which, despite a high surfactant concentration, are preferably still pumpable or pourable. By virtue of their ready biodegradability, these water-based mixtures are readily infested by such microbes as bacteria and fungi, so that the quality and, in particular, stability in storage of the surfactant mixtures can be adversely affected. Although there are a number of useful antimicrobial agents which prevent microbial infestation and guarantee adequate stability in storage, the use of preservatives, such as glutaraldehyde or benzoic acid for example, is not without technical problems. Thus, there is a danger that the presence of such preservatives may cause discoloration of the surfactant paste during storage. On the other hand, the presence of preservatives is not accepted by the next user for all applications of the surfactant pastes.

DESCRIPTION OF THE INVENTION

It has now been found that water-based surfactant pastes protected against microbial infestation can have excellent stability in storage, even in the absence of the usual preservatives, providing measures are taken to ensure that certain impurities are not present during their formulation.

These requirements are satisfied by a water-based surfactant paste containing 30 to 70% by weight of a surfactant stable in alkaline medium, more particularly a nonionic surfactant of the alkyl glycoside type, characterized in that the paste is substantially free from bleachable colour bodies and precursors thereof which lead to discoloration in alkaline medium and is substantially free from secondary products and residues which reduce the pH value during storage by alkali consumption and in that the paste has a pH value of at least 11, preferably in the range from 11 to 12.5 and, more preferably, of at least 11.5 through the presence of added alkaline substances.

It has surprisingly been found that, even after storage for several months at 40° to 50° C., the product according to the invention is stable in color and is free from microbial infestation and, hence, does not require additional chemical stabilization.

Surfactants stable in alkaline medium are understood to be surface-active compounds, such as alkoxylated long-chain alcohols, more particularly fatty alcohol ethoxylates, including compounds containing closed terminal groups, surfactants such as alkylether carboxylic acids, fatty alcohol sulfates and ether sulfates, alkanesulfonates and, in particular, surfactants of which the hydrophilic part derives from carbohydrate compounds. Surfactants of the alkyl glycoside type are particularly preferred. Surfactants of this type are understood to be mixtures of alkyl monoglycosides and alkyl oligoglycosides of the type obtained in the acid-catalyzed reaction of sugars and alkanols.

The particularly preferred alkyl glycosides are nonionic surfactants of the type known, for example, from U.S. Pat. Nos. 3,547,828 and 3,839,318. Production processes for particularly light-colored and color-stable alkyl glycosides are described in European patent applications EP 0 301 298 A1, EP 0 362 671 A1 and EP 0 357 969 A1. The alkyl component of the alkyl glycosides generally consists of aliphatic residues containing 8 to 24 and, more particularly, 8 to 18 carbon atoms. The corresponding fatty alkyl radicals obtainable from fats as renewable raw materials by way of the fatty alcohols are particularly preferred. Alkyl radicals derived from synthetic primary alcohols, more particularly from the so-called oxo alcohols, are also suitable in principle, but are less preferred in the present case. The sugar component in the alkyl glycoside may emanate from typical aldoses or ketoses, such as for example glucose, fructose, mannose, galactose, talose, gulose, allose, altrose, idose, arabinose, xylose, lyxose and ribose. By virtue of the abundantly available raw materials glucose or starch or starch degradation products, glucose is the particularly preferred sugar component. The average degree of oligomerization of the alkyl glycosides present in the pastes according to the invention may assume any value from the point of view of paste stability, i.e. it may be in the typical range of 1.2 to 3.0. This average degree of oligomerization is based on the quantity of alkyl monoglycoside and alkyl oligoglycoside surfactant in the alkyl glycoside product. However, it is preferred to use alkyl glycosides in which the degree of oligomerization is distinctly below 1.5 and, more particularly, in the range from 1.3 to 1.4, the associated fatty alkyl radical essentially being around $C_{12}$. Different quantities of $C_{8-10}$ and $C_{14-16}$ may be present, depending on the width of the cut. These alkyl glycosides are distinguished by particularly good surfactants properties. Together with water and the alkaline substances, they represent a particularly preferred embodiment of the invention. Other preferred embodiments are based on C chain cuts centered around $C_{8/10}$ and around $C_{14/16}$. The former have very good solubilizing properties while the latter are suitable as wetting agents and emulsifiers.

The "surfactant paste" is a paste in a viscosity range extending from flowable to viscous. Accordingly, the viscosities (as measured using a Höppler viscosimeter at 40° C. or a Brookfield Helipath viscosimeter at 40° C./4 r.p.m.) are in the range from about 1,000 to 100,000.

The surfactants present in the water-based surfactant paste, more particularly the alkyl glycosides, are substantially free from bleachable pigments, pigment precursors, secondary products and residues adversely affecting color quality where these surfactants have been subjected to a bleaching process after their production. The bleaching process in question is preferably an oxidative bleaching process, more particularly using hydrogen peroxide as the oxidizing agent. This bleaching process is preferably carried out in the presence of magnesium cations which may enter the system either in the form of alkaline magnesium compounds, such as the oxide, hydroxide, carbonate, or an alcoholate to neutralize the acidic catalyst at the end of the production process in the case of the alkyl glycosides. However, it is also sufficient if neutralization is carried out with typical alkalis, more particularly alkaline sodium compounds, at the end of the surfactant production process and water-soluble or insoluble magnesium compounds, for example those mentioned above, are subsequently added in such a quantity that the subsequent bleaching step takes place in the presence of 100 to 1,000 ppm magnesium. If steps are taken in the bleaching process to ensure that a high pH value of at least 9 and preferably at least 10 is maintained, the residual peroxide content can be reduced to values of at most 50 to 100 ppm $H_2O_2$ in the final stage of the bleaching process by heat treatment of the paste at 80° to 150° C. The oxidatively bleached products may be after-treated with reducing agents; the pH value should not fall below 8.5 during the reductive-aftertreatment. The surfactant paste thus treated acquires the high pH value according to the invention by compensation of the consumption of alkali observed during bleaching by addition of sodium hydroxide, potassium hydroxide or sodium or potassium carbonates and adjustment of the desired pH value.

Accordingly, the present invention also relates to a process for the production of the storable aqueous surfactant paste, more particularly an alkyl glycoside paste, of the type obtained by the typical production processes for alkali-stable surfactants, more particularly alkyl glycosides, after the additional bleaching with aqueous $H_2O_2$, the bleaching process being carried out as oxidative bleaching with $H_2O_2$ in the presence of magnesium compounds in alkaline medium at pH values above pH 9 and preferably above pH 10, characterized in that, after the residual peroxide content has been reduced to values of at most 50 to 100 ppm $H_2O_2$, the pH is adjusted to a value of at least 11, preferably in the range from 11 to 12.5 and, more preferably, at least 11.5 by addition of alkalis, more particularly alkaline compounds whose presence does not affect the subsequent use of the surfactant paste or is desirable, more particularly sodium hydroxide, potassium hydroxide or sodium or potassium carbonates, the water content of the pastes being adjusted to a value in the range from 30 to 70%.

Where present in the particularly preferred form of alkyl glucoside pastes, the water-based surfactant pastes according to the invention produced in this way can be mixed with additional surfactants otherwise made stable to alkalis to obtain a product which contains a surfactant mixture in compounded form which is particularly suitable for subsequent processing or whereby the viscosity and flow behavior of the paste during storage are promoted.

To produce the stabilized paste according to the invention, the process steps of peroxide bleaching, peroxide degradation, optionally reductive aftertreatment and pH adjustment may be carried out continuously or discontinuously. The bleaching step and the peroxide degradation step are preferably carried out continuously, more particularly in cascades of stirred tanks with suitable temperature and residence time parameters. For example, the peroxide bleaching step is carried out with $H_2O_2$ at 110° C. over an average residence time of 2 hours, which leaves a residual peroxide value of about 300 to 600 ppm $H_2O_2$. In the subsequent peroxide degradation step, the mixture is kept at 120° C. for an average time of 3 hours, leaving a residual peroxide content of 30 to 70 ppm.

EXAMPLES

EXAMPLE 1

The microbially stable alkaline version was produced from 100 kg of a reaction mixture prepared by reaction of dodecanol with glucose in a molar ratio of 5: 1. The mixture contained approx. 27.5% alkyl glucoside and 0.2% catalyst (p-toluene sulfonic acid). Working up was carried out as follows:

The catalyst was neutralized by addition of 100 g of 50% sodium hydroxide at 90° C.

15 g finely divided magnesium oxide were then stirred in.

The mixture was concentrated by evaporation to 1% residual fatty alcohol in a thin-layer evaporator at 1 mbar and at a heat carrier temperature of 200° C. Approx. 28 kg distillation residue were obtained.

By addition of fully deionized water, the residue was converted into approx. 56 kg of a water-based paste.

The paste was then bleached for 1 hour at 110° C. in a pressure reactor by addition of 300 g $H_2O_2$ (1,000 g 30% solution) and 420 g NaOH (840 g 50% solution). Vacuum degassing left a light yellow product containing approx. 350 ppm residual hydrogen peroxide.

The product was thermally aftertreated for another 3 hours at 120° C. The residual peroxide content fell to less than 50 ppm without any significant change in the color of the product.

The paste obtained had a pH value of 11.5 which remained stable after storage for 4 months at 60° C. In a microbial infestation test with $10^6$ bacteria and $10^5$ fungi/g, the product produced destruction times of at most 3 days for bacteria and at most 14 days for fungi over the entire storage period. (Bacterial mixture: *Staphylococcus aureus, Enterococcus faecium, Escherichia coli, Enterobacter aerogenes, Pseudomonas aeruginosa.* Fungal mixture: *Candida albicans, Aspergillus niger, Penicillium rubrum, Trichoderma viride*).

The paste had a viscosity of 1,800 mPa.s at 40° C., as measured in accordance with DIN 53015.

EXAMPLE 2

100 kg of a reaction mixture obtained by reaction of glucose with $C_{12/14}$ fatty alcohol (75/25%) in a molar ratio of 1:4.5, alkyl glycoside content 29%, was worked up as follows:

The catalyst (0.2% p-toluene sulfonic acid) was neutralized with 110 g 50% sodium hydroxide.

20 g finely divided MgO were stirred in.

Distillation was carried out as in Example 1 and produced approx. 30 kg APG residue.

After preparation of a 50% water-based paste, the paste was bleached for 2 hours at 105° C. with addition of 400 g $H_2O_2$ (1,330 g 30% solution) and 300 g NaOH (600 g 60% solution).

The thermal aftertreatment was carried out over a period of 6 hours at 105° C., the residual peroxide content falling to less than 50 ppm.

The product was degassed in vacuo. The pH value was adjusted to 11.8 by addition of another 300 g NaOH (as 600 g 50% solution).

After storage for 4 months, the product was color-stable, the pH value remained constant at 11.8 and the microbial stability corresponded to that of the sample of Example 1. Viscosity of the paste: 2,000 mPa.s (measured as in Example 1).

What is claimed is:

1. In a process for stabilizing an aqueous paste of an alkyl glycoside surfactant against microbial infestation, the improvement wherein following oxidative bleaching of the paste with hydrogen peroxide, the unreacted hydrogen peroxide is reduced to a value of at most 100 ppm $H_2O_2$, and the pH thereof is then adjusted to a value of at least 11, and wherein the water content of the paste is adjusted to a value in the range of from about 30 to about 70% by weight.

2. The process of claim 1 wherein the pH is adjusted by the addition of sodium hydroxide, potassium hydroxide, sodium carbonate, or potassium carbonate.

3. The process of claim 1 wherein said alkyl glycoside is a $C_{2-18}$ alkyl glycoside having a degree of oligomerization of from about 1.3 to about 3.0.

4. The process of claim 3 wherein said degree of oligomerization is from about 1.3 to about 1.4.

5. The process of claim 1 wherein said paste is further comprised of an additional surfactant which is stable at a pH of at least 11.

6. The process of claim 1 wherein said pH is at least about 11.5.

7. The process of claim 1 wherein the unreacted hydrogen peroxide is reduced to a value of at most 50 ppm and the pH is adjusted in the range of from 11 to 12.5.

8. The process of claim 1 wherein the aqueous paste also contains from about 100 to about 1000 ppm of magnesium cations.

9. The process of claim 1 wherein said aqueous paste is substantially free from bleachable pigments, pigment precursors, and secondary products and residues that adversely affect color quality.

10. The process of claim 1 wherein the bleached paste is treated with a reducing agent prior to said pH adjustment.

11. A process for the production of an aqueous surfactant paste, stabilized against microbial infestation, containing an alkyl glycoside surfactant which is stable in alkaline medium comprising the steps of:

A) bleaching an alkyl glycoside surfactant with hydrogen peroxide to form a bleached paste;

B) reducing the hydrogen peroxide content of said bleached paste to a value of at most 100 ppm;

C) adjusting the pH of the bleached paste to a value of at least 11; and

D) adjusting the water content of the bleached paste as needed to a level of from about 30 to about 70% by weight.

12. The process of claim 11 wherein said paste in step A) is further comprised of from about 100 ppm to about 1000 ppm of magnesium cations.

13. The process of claim 11 wherein said alkyl glycoside is a $C_{8-18}$ alkyl glycoside having a degree of oligomerization of from about 1.3 to about 3.0.

14. The process of claim 13 wherein said degree of oligomerization is from about 1.3 to about 1.4.

15. The process of claim 11 wherein said paste in step A) is further comprised of an additional surfactant which is stable at a pH of at least 11.

16. The process of claim 11 wherein said pH in step C) is at least about 11.5.

17. The process of claim 11 wherein step A) is carried out at a temperature of from about 105° C. to about 110° C.

18. The process of claim 11 wherein in step B) the hydrogen peroxide content is reduced to a value of at most 50 ppm and in step C) the pH is adjusted in the range of from 11 to 12.5.

19. The process of claim 11 wherein said aqueous paste is substantially free from bleachable pigments, pigment precursors, and secondary products and residues that adversely affect color quality.

20. The process of claim 19 wherein said pH is adjusted to a value of at least 11.5.

21. The process of claim 11 wherein prior to step C) the bleached paste is treated with a reducing agent.

* * * * *